US012805993B2

(12) United States Patent
Gottenbos

(10) Patent No.: US 12,805,993 B2
(45) Date of Patent: Nov. 24, 2026

(54) ORAL CARE DEVICE ADAPTED TO REDUCE GAG REFLEX

(71) Applicant: KONINKLIJKE PHILIPS N.V., Eindhoven (NL)

(72) Inventor: Bart Gottenbos, Budel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 400 days.

(21) Appl. No.: 18/267,168

(22) PCT Filed: Dec. 1, 2021

(86) PCT No.: PCT/EP2021/083719
§ 371 (c)(1),
(2) Date: Jun. 14, 2023

(87) PCT Pub. No.: WO2022/128467
PCT Pub. Date: Jun. 23, 2022

(65) Prior Publication Data

US 2024/0050214 A1 Feb. 15, 2024

Related U.S. Application Data

(60) Provisional application No. 63/126,301, filed on Dec. 16, 2020.

(51) Int. Cl.
*A61C 17/22* (2006.01)
*A61C 1/04* (2006.01)
(Continued)

(52) U.S. Cl.
CPC .......... *A61C 17/225* (2013.01); *A61C 17/228* (2013.01); *A61C 19/06* (2013.01); *A61N 1/0456* (2013.01)

(58) Field of Classification Search
CPC ..... A61C 17/225; A61C 17/228; A61C 19/06; A61N 1/0456
See application file for complete search history.

(56) References Cited

U.S. PATENT DOCUMENTS 2,969,059 A * 1/1961 Cicero ..................... A61B 1/24 600/242
4,672,959 A * 6/1987 May ..................... A63B 71/085 128/861

(Continued)

FOREIGN PATENT DOCUMENTS

CN 111265323 A * 6/2020 ......... A61C 17/0211
CN 113518598 A * 10/2021 ........... A61C 17/028

(Continued)

OTHER PUBLICATIONS

International Search Report and Written Opinion Dated Mar. 10, 2022 For International Application No. PCT/EP2021/083719 Filed Dec. 1, 2021.

(Continued)

*Primary Examiner* — Marc Carlson

(57) ABSTRACT

Gag reflex when a mouthpiece of an oral care device contacts the posterior oral cavity is reduced by provision of a projection on the handpiece that contacts the user's skin in such a way that gag reflex is reduced or eliminated due to stimulation of nerves in the user's face. In an embodiment, the projection has a tip that contacts the user's face on or near the groove between the lower lip and the chin, exerting mechanical pressure, vibration, or electrical stimulation, which stimulates nerves to reduce the gag reflex.

13 Claims, 7 Drawing Sheets

(51) Int. Cl.
*A61C 19/06* (2006.01)
*A61N 1/04* (2006.01)

(56) References Cited

U.S. PATENT DOCUMENTS

| | | | | | |
|---|---|---|---|---|---|
| 12,263,293 | B2 * | 4/2025 | Fulton, III | A61B 1/24 | |
| 2008/0230055 | A1 * | 9/2008 | NaPier | A61M 16/0497 | 128/200.26 |
| 2009/0292228 | A1 * | 11/2009 | Van Kuren | A61H 39/00 | 601/84 |
| 2014/0216470 | A1 * | 8/2014 | Buttaravoli | A61M 16/0463 | 128/861 |
| 2019/0374812 | A1 * | 12/2019 | McGhee | A63B 21/023 | |
| 2020/0376261 | A1 * | 12/2020 | Stevens | A61N 1/0456 | |
| 2021/0085436 | A1 * | 3/2021 | Evans | A61C 17/0211 | |
| 2022/0313409 | A1 * | 10/2022 | Pai | A46B 9/045 | |
| 2025/0170349 | A1 * | 5/2025 | Smith | A61B 90/00 | |

FOREIGN PATENT DOCUMENTS

| | | | | | |
|---|---|---|---|---|---|
| DE | 202020101826 | U1 | * | 6/2021 | A61N 5/067 |
| WO | WO-2009127947 | A2 | * | 10/2009 | A61M 11/00 |
| WO | WO-2020047659 | A1 | * | 3/2020 | A61N 7/00 |
| WO | 2020214697 | A | | 10/2020 | |
| WO | WO-2020214722 | A1 | * | 10/2020 | A61F 5/56 |

OTHER PUBLICATIONS

Kazunori Fujiwara et al; “Novel mouthpiece for reducing the gag reflex during esophagogastroduodenoscopy”; digestive endoscopy 2020; 32; 534-540.

* cited by examiner

ORAL CARE DEVICE ADAPTED TO REDUCE GAG REFLEX

This application is the U.S. National Phase application under 35 U.S.C. § 371 of International Application No. PCT/EP2021/083719, filed on Dec. 1, 2021, which claims the benefit of U.S. Application Ser. No. 63/126,301, filed Dec. 16, 2020. These applications are hereby incorporated by reference herein.

FIELD OF THE INVENTION

The invention is related generally to the field of devices for oral care and oral care devices which include a mouthpiece.

BACKGROUND OF THE INVENTION

Some oral care devices include mouthpieces. Mouthpiece toothbrushes, for example, include a mouthpiece which covers the upper and lower dental arch. Bristles projecting from the inner surfaces of the mouthpiece brush the teeth when the mouthpiece is subjected to vibrational energy from the handpiece to which it is coupled. In order to ensure all tooth surfaces are cleaned, the mouthpiece must extend far enough into the oral cavity to clean the rearward most molars.

A roadblock to widespread acceptance of these devices is user discomfort. A key concern for discomfort of mouthpiece toothbrushes is the gag-reflex. When the mouthpiece touches the posterior parts of the oral cavity, the gag reflex can be triggered. This will cause substantial discomfort when using the device.

SUMMARY

Embodiments of the invention aim to reduce the occurrence of the gag reflex when a mouthpiece of an oral care device contacts the posterior oral cavity. They solve the problem of how to provide a device with a mouthpiece that extends to the posterior of the mouth while not inducing a gag reflex, or substantially reducing the gag reflex that would otherwise be caused by the mouthpiece The embodiments solve this problem by providing a mouthpiece with means to stimulate nerve endings and/or apply pressure on pressure points on the user's face or elsewhere on the user's body. Stimulation of nerves on certain parts of the face or body and/or pressure on certain pressure points, such as the pressure points in the area of the groove between the lower lip and the chin, can reduce the gag reflex. Embodiments of the invention use this principle to make the use of a mouthpiece for teeth cleaning or other purposes more comfortable.

According to examples of embodiments of the invention, there is provided an apparatus for use with a mouthpiece which is inserted into a user's mouth during use, which includes an extension extending outward from the mouthpiece to the exterior of the mouth; a member which extends from the extension to a location where its end is in contact with the skin of the user while the mouthpiece is inserted into the user's mouth. In some embodiments, the extension and the member may be constructed as a unitary piece.

In some embodiments, the mouthpiece is a tooth cleaning device. In these embodiments, the extension may include a housing that contains a power source and/or a vibratory motion device, and a coupling which connects this assembly to the mouthpiece. The vibratory motion device may be, for example, an eccentric mass motor. By coupling the vibratory motion device to the tooth cleaning mouthpiece, a vibrating motion is imparted to the mouthpiece, which enables cleaning by the mouthpiece. In such an embodiment, the member may be an arm extending from the housing.

In an embodiment, the end of the member contacts an area of a user's face between the user's lower lip and bottom of the chin when in use. In an embodiment, the end of the member includes a tip having raised areas, or bumps, on its surface.

In some embodiments, the end of the member includes a plurality of fibers. With the fibers in contact with the user's skin, nerve stimulation is provided to the user. The fibers may move in response to the vibratory motion device, resulting in the fibers providing a stroking motion on the user's skin. The fibers may make up a part of the extension's length. For example, the fibers may be mounted on an arm that extends part of the way between the extension and the user's skin, with the fibers reaching from the arm and extending to the skin. In this example, the arm and fibers together make up the extension. In another example, the fibers may make up the entirety of the extension.

In some embodiments, the length and/or shape of the member is adjustable. This allows the member to accommodate differing anatomies. It also gives the user a way to place the end of the member on the location of his skin that is perceived as most comfortable and/or effective. Also, if for some reason the user desires that the member not touch his or her skin (for example, if a user chooses to not use the gag reflex reducing aspect of a tooth cleaning device), in some embodiments the adjustability may allow the user to arrange the member so that it does not touch the skin.

Adjustability of the length and/or shape of the member may be provided by forming the member from an elastomeric deformable material. In another embodiment, adjustability is provided by a compressible spring that lies in the path from the end of the member to the point where it is attached to the extension which, in some embodiments, is a housing. In another embodiment, the member includes a cylinder, a shaft arranged to slide within the shaft, and a spring acting between an end of the cylinder and the shaft. In embodiments with springs, the springs may be chosen for a stiffness that maintains contact between the end of the member and the user's skin.

In another embodiment, the member includes electrodes in electrical communication with a power source. The electrodes are capable of being positioned where they will be in contact with the user's skin, to supply electrical stimulation to the user's nerves. In embodiments such as these, the electrodes may be mounted on an arm extending from the extension, or they may be attached by electrically conducting wires to the extension. The electrodes may be mounted in such a way that they are easily removed and replaced when needed.

In an embodiment, a method for producing a device capable of stimulating nerves on the face of a user of a mouthpiece includes attaching to the mouthpiece an extension which protrudes from the mouthpiece to the exterior of the face; and providing a member piece which extends from the extension to a location where its end is capable of contacting the skin of the user while the mouthpiece is inserted into the user's mouth. In an example, this method may include the step of forming the member of a compressible material. In another example, the method may further include the step of providing an electrical power source within the extension and an electrical path from the power source through the member to its end.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the inventive subject matter.

DETAILED DESCRIPTION

Figure 1:
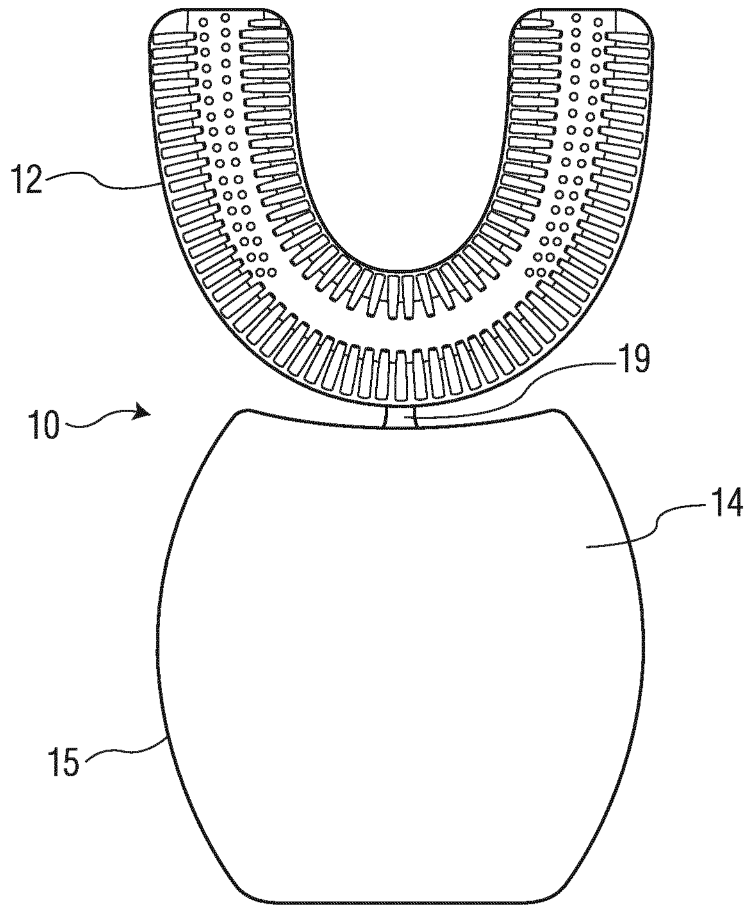
FIG. 1 is a top view of a mouthpiece toothbrush device.
Figure 3:
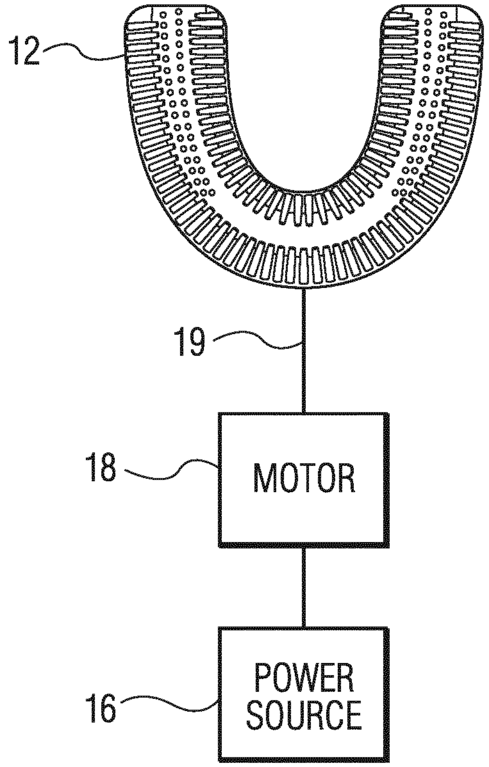
FIG. 3 is a schematic representation of the mouthpiece toothbrush device of FIG. 1.

Embodiments of the invention will be described in the context of an oral hygiene device. This is for illustrative purposes only, and should not be construed as limiting the invention to this context. Referring to FIGS. 1 and 3, a mouthpiece toothbrushing device 10 includes a mouthpiece 12 coupled to a handpiece 14. The mouthpiece 12 may include a trough for the upper dental arch, and a trough for the bottom arch, each of which have bristles extending inwardly to engage tooth surfaces In use, the mouthpiece 12 is inserted into the oral cavity, the upper and lower dental arches are positioned within the troughs, and the mouthpiece 12 is held between the upper and lower teeth. The ends of the mouthpiece 12 extend toward the back of the oral cavity.

The handpiece 14 includes a housing 15 which contains a power source 16 and electronics, including a motor 18. The handpiece 14 has a size and shape which allows it to be used as a handle for the device 10. While a particular example of a handpiece for a mouthpiece toothbrush is shown in the drawings and described for the purpose of illustration, it will be understood that any element which is attached to a mouthpiece and extends outward from the mouth may act as a handpiece.

In the illustrated embodiment, the electronics inside the handpiece 14 include a source of vibration, such as for example, an eccentric mass motor 18, which is coupled to the mouthpiece 12 through a coupling 19 to cause the mouthpiece 12 and its bristles to vibrate in a way that results in cleaning of the teeth. The electronics also includes an on/off switch for the motor 18.

Figure 2:
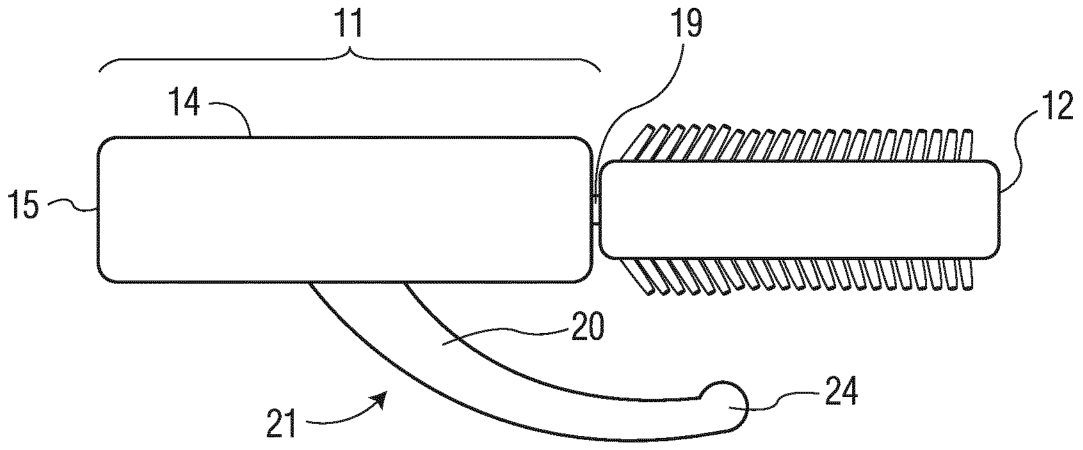
FIG. 2 a side view of an embodiment.

In the embodiment of FIG. 2, the handpiece 14 together with the coupling 19 form an extension 11 extending outward from the mouthpiece 12 and the user's lower lip 17 (see, for example FIG. 4) to the exterior of the face. In other embodiments, the extension 11 may take other forms. For example, the extension may be a stem, a handle, a small piece protruding from the mouthpiece, or another form protruding from the mouthpiece 12 so as to extend outward from the mouthpiece when in use. It may be formed of a separate piece attached to the mouthpiece, or may be unitary with the mouthpiece 12.

Figure 6:
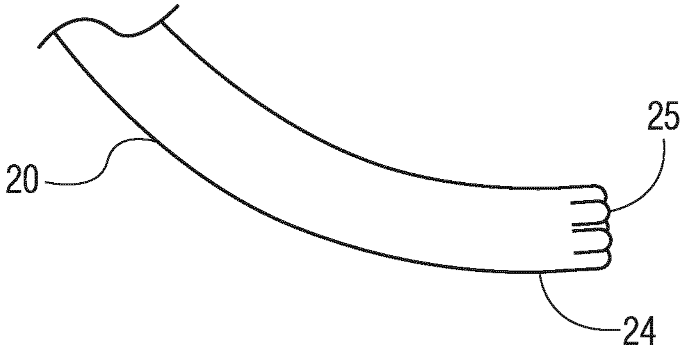
FIG. 6 is a side view of the face-contacting tip of an embodiment.
Figure 7:
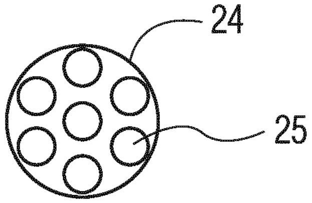
FIG. 7 is an end view of the face-contacting tip of FIG. 6.

Referring to FIG. 2, in the illustrated embodiment a member 21, which can take the form of an arm 20, extends from the handpiece 14 toward an area 22 of the user's face between the lower lip 17 and chin 23 when the mouthpiece is in position for usage. A tip 24 on the end of the arm 20 contacts the user's skin in this area 22 when the mouthpiece 12 is positioned for use between the teeth 25*a*, 25*b*. This facial area 22 is the general area of the mentolabial sulcus, or labiomental fold. Referring to FIGS. 6 and 7, the skin contacting area of the tip 24 may be include one or more bumps of raised areas 26, to increase local pressure applied to the face by effectively reducing the area over which pressure from the arm 20 is applied.

In the embodiment shown in FIG. 2, the member 21 is a rigid arm 20. In other embodiments, the arm 20 may be configured to adapt to anatomical differences between individuals by adapting its length and/or shape over a certain range. In this embodiment, "shape" includes the curvature of the member and the angle it makes with the extension 11. This may be accomplished by forming the arm 20 out of a material that is capable of deforming elastically over a desired range. In such an embodiment, the arm 20 may compress when the device 10 is placed in its usage position if its length must be shortened in order to adapt to a particular user's anatomy. Alternatively, the material of the arm 20 may be chosen so that the user can alter the shape of the arm 20 as desired for the tip 24 to contact the desired area of the user's face. Materials for these examples may be chosen from commercially available materials with the desired properties.

Figure 4:
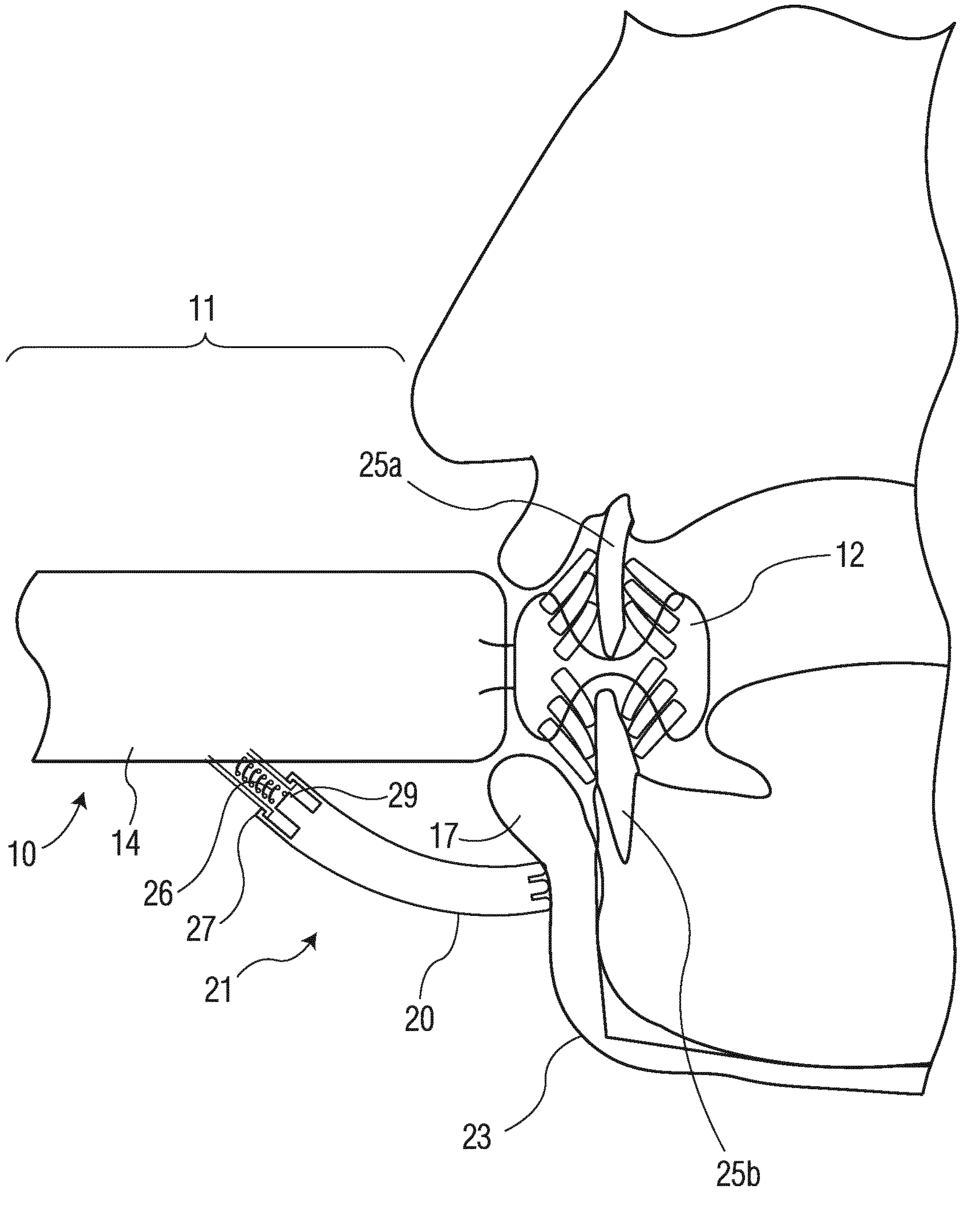
FIG. 4 is a side view of an embodiment positioned for use with a mouthpiece in a user's oral cavity, partially cutaway.
Figure 5:
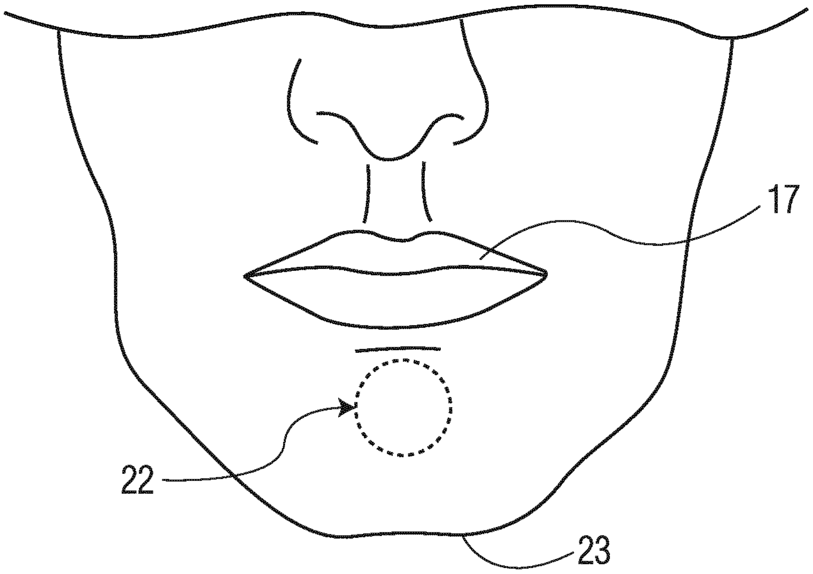
FIG. 5 is an illustration of a portion of a face.

In another embodiment illustrated in FIG. 4, the length of the member 21 is provided with a length adjustment mechanism. This length adjustment may be provided by a cylinder 22 having a shaft 29 arranged to slide within the cylinder, with a spring 26 acting between an end of the cylinder and the shaft, so as to adjust the length of the member 20.

Figure 8:
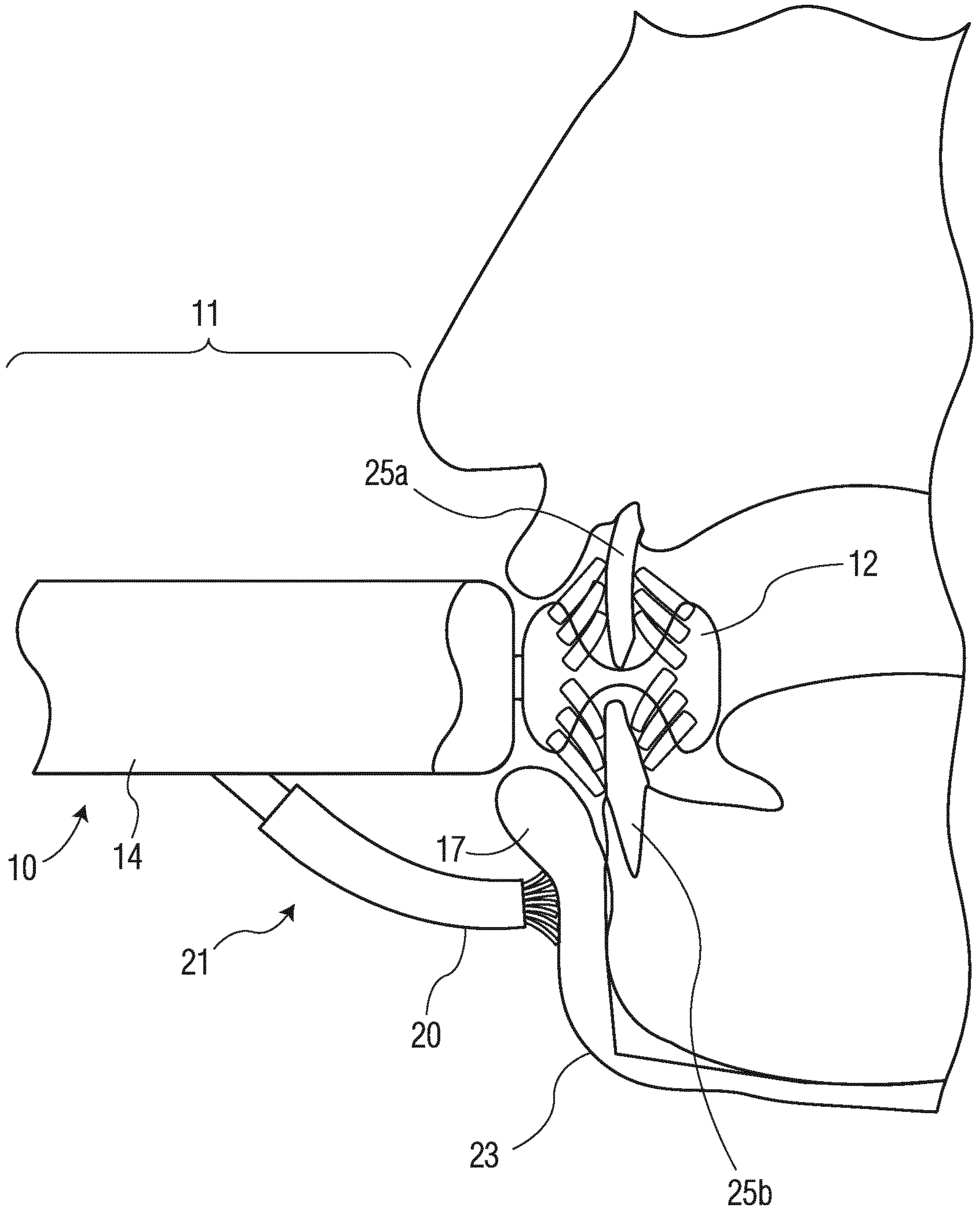
FIG. 8 is a side view of another embodiment positioned for use with a mouthpiece in a user's oral cavity, partially cutaway.

In the embodiments described above, application of pressure to the region 22 of the user's face provides stimulation to nerves in this area, which results in a reduced gag reflex. Other nerve stimulating modes may be employed, such as stroking the skin or tingling. Referring to FIG. 8, in an embodiment where the handpiece 14 will vibrate due to the vibratory action of the motor 18, a tingling sensation within the facial area 22 may be provided by attaching bristles or other thin fibers 28 to the end of an arm 20. In the illustrated embodiment, the arm 20 does not extend the entire distance from the handpiece 14 to the skin. Instead, the arm plus the fibers 28 mounted on its end would together form the member reaching from the extension to the skin.

The fibers 28 may be of a length and material that allows them to provide the adaptation to differing anatomies, the fibers being flexible enough to accommodate different face shapes. In such an embodiment, an additional length adjustment mechanism such as spring system would not be needed. The arrangement of fibers 28 on the arm may be a single circular tuft, an arrangement of a plurality of tufts, or other arrangements of fibers. The fibers 28 may be arranged around a tip of the extension, to provide fiber stroking with pressure from the tip of a rigid or adjustable arm as described above. In other embodiments, the fibers 28 may be mounted directly onto the extension 11, in which case the fibers themselves would make up the entire length of the extension.

While the area between the lower lip 17 and chin 23 is used in the illustrated embodiments to influence gag reflex, other stimulation points on the skin, such as the nose or other facial areas, may be stimulated by extensions which reach from the extension protruding from the user's lips, such as the illustrated handpiece 14 plus coupler 19 assembly, to one or more of these areas.

Figure 9:
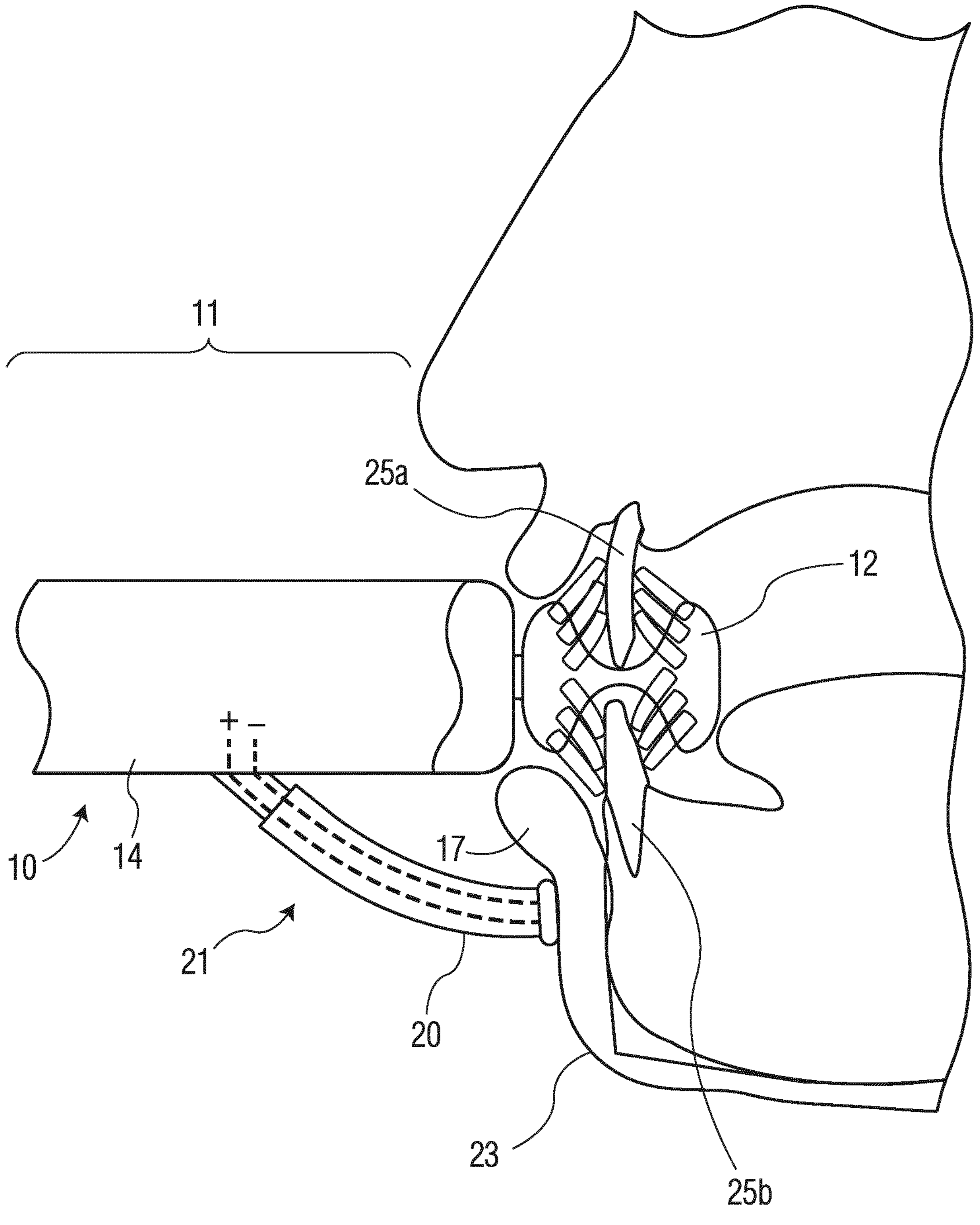
FIG. 9 is a is a side view of another embodiment positioned for use with a mouthpiece in a user's oral cavity, partially cutaway.
Figure 10:
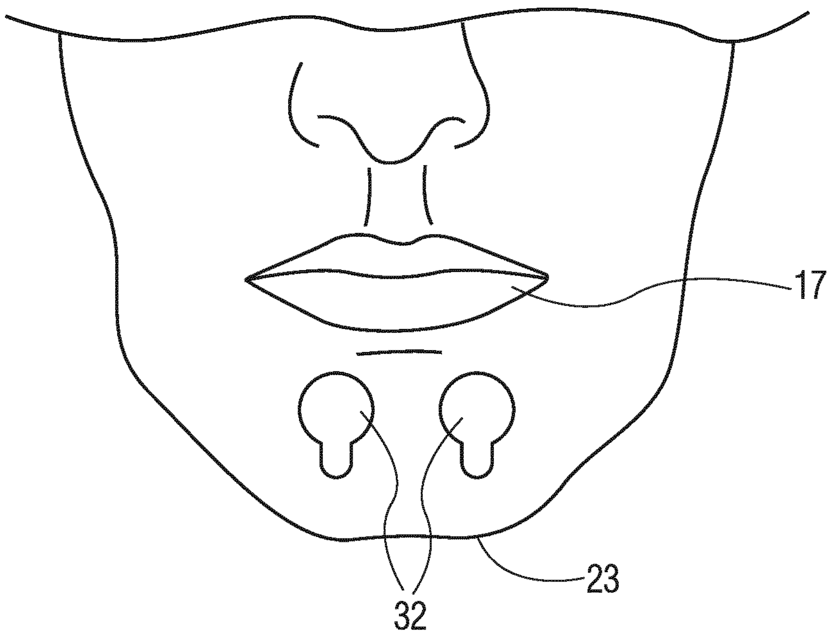
FIG. 10 is an illustration of a placement of electrodes in the embodiment of FIG. 9 in use.

In another embodiment illustrated in FIGS. 9 and 10, electrical stimulation is used in the area 22 of the face. Electrical nerve stimulation, commonly known as trans-epidermal nerve stimulation or TENS, works by a similar mechanism as mechanical stimulation, by loading the nerve system with signals which limit other signals, such as pain signals or gag reflex signals getting to the brain. As an example, an electrical signal could be conducted from a power source 16 in the handpiece 14 through electrically conducting wires 31 in the arm to a pair of electrodes 32 on the tip 24. The electrodes 32 may be mounted on the tip itself, or may be connected with a pair of wires protruding from the tip or from the housing 15 so as to allow the user to position the electrodes on the face as desired. In embodiments where electrodes are mounted on the tip, the tip will have a shape and sized as needed to accommodate the electrodes. Alternatively, the arm may have two branches with two tips, each bearing an electrode.

As shown in FIG. 10, the electrodes 32 may be positioned at or near the area 22 between the lower lip and chin. The electrodes may be TENS electrodes made with conductive hydrogels. The electrodes may be removable from the device in a manner like commercially available TENS electrodes, to allow for their replacement when needed.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the mouthpiece device is an orthodontic device, a whitening device, or other dental therapeutic or cosmetic device. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single unit may fulfill the functions of several items recited in the claims. The mere fact that certain measures are recited in mutually different dependent claims does not indicate that a combination of these measured cannot be used to advantage. Any reference signs in the claims should not be construed as limiting the scope of the claims.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The invention claimed is:

1. An apparatus for use with a mouthpiece which is inserted into a user's mouth during use, comprising:

an extension which extends outward from the mouthpiece;

a member having an end and extending from the extension to a location where the end is in contact with the skin of the user while the mouthpiece is inserted into the user's mouth, wherein the end of the member comprises a tip having a plurality of raised areas on its surface.

2. The apparatus of claim 1 wherein the mouthpiece is a tooth cleaning device.

3. The apparatus of claim 2 wherein the extension comprises a housing containing a power source and/or a vibratory motion device.

4. The apparatus of claim 3 wherein the member comprises an electrode in electrical communication with the power source.

5. The apparatus of claim 1 wherein the end of the member contacts an area of a user's face between the user's bottom lip and chin when in use.

6. The apparatus of claim 1 wherein the end of the member comprises a plurality of fibers.

7. The apparatus of claim 1 wherein the length and/or shape of the member is adjustable.

8. The apparatus of claim 7 wherein the member comprises an elastomerically deformable material.

9. The apparatus of claim 7 wherein the member comprises a compressible spring.

10. The apparatus of claim 7 wherein the member comprises a cylinder, a shaft arranged to slide within the shaft, and a spring acting between an end of the cylinder and the shaft.

11. The apparatus of claim 1, wherein the member comprises a plurality of fibers.

12. A method for producing a device capable of stimulating nerves on the face of a user of a mouthpiece comprising:

attaching to the mouthpiece an extension extending from the mouthpiece;

providing a member extending from the extension to a location where its end is capable of contacting the skin of the user while the mouthpiece is inserted into the user's mouth; and forming the member of a compressible material.

13. The method of claim 12 further comprising the step of providing an electrical power source within the extension and an electrical path from the power source through the member to its end.

* * * * *